(12) United States Patent
Savaiano

(10) Patent No.: US 6,279,577 B1
(45) Date of Patent: Aug. 28, 2001

(54) SUPPORTER

(76) Inventor: Carl A. Savaiano, 1601 Colorado Ave. South, St. Louis Park, MN (US) 55416

( * ) Notice: Subject to any disclaimer, the term of this patent is extended or adjusted under 35 U.S.C. 154(b) by 0 days.

(21) Appl. No.: 09/467,338

(22) Filed: Dec. 20, 1999

Related U.S. Application Data

(60) Provisional application No. 60/113,073, filed on Dec. 21, 1998.

(51) Int. Cl.⁷ ........................................... A61F 5/56
(52) U.S. Cl. ........................ 128/848; 128/857; 602/902
(58) Field of Search ..................... 128/846, 848, 128/859–862; 602/902, 17, 18

(56) References Cited

U.S. PATENT DOCUMENTS

| | | |
|---|---|---|
| D. 331,115 | 11/1992 | Stout . |
| D. 410,089 | 5/1999 | Schiavoni . |
| 649,896 * | 5/1900 | Baughman ............................ 128/848 |
| 904,760 | 11/1908 | Cutting . |
| 1,113,732 | 10/1914 | Archibald . |
| 1,216,679 | 2/1917 | Foster . |
| 1,587,558 * | 6/1926 | Sheffield ............................ 128/848 |
| 1,629,892 * | 5/1927 | Storms ................................ 128/848 |
| 1,990,411 | 2/1935 | Lowry . |
| 2,294,066 | 8/1942 | Baehler . |
| 2,711,730 | 6/1955 | Rogers . |
| 3,312,217 | 4/1967 | McKinstry . |
| 5,031,609 | 7/1991 | Fye . |
| 5,687,743 * | 11/1997 | Goodwin ............................ 128/848 |
| 5,787,894 * | 8/1998 | Holt .................................... 128/848 |
| 5,834,004 | 11/1998 | Lavore . |
| 5,893,365 | 4/1999 | Anderson . |

* cited by examiner

Primary Examiner—Michael A. Brown

(57) ABSTRACT

A human body appendage supporter has elastic members that apply pressure to the appendage to retain the appendage in a desired position. The supporter is a one-piece structure having elastic side straps joined to one or more elastic top members and a pair of elastic bottom members. The supporter when placed on a person's head with the elastic members around the chin and the top members over the top of the person's head biases the person's mouth closed so that air flows through the nasal airway passages.

18 Claims, 5 Drawing Sheets

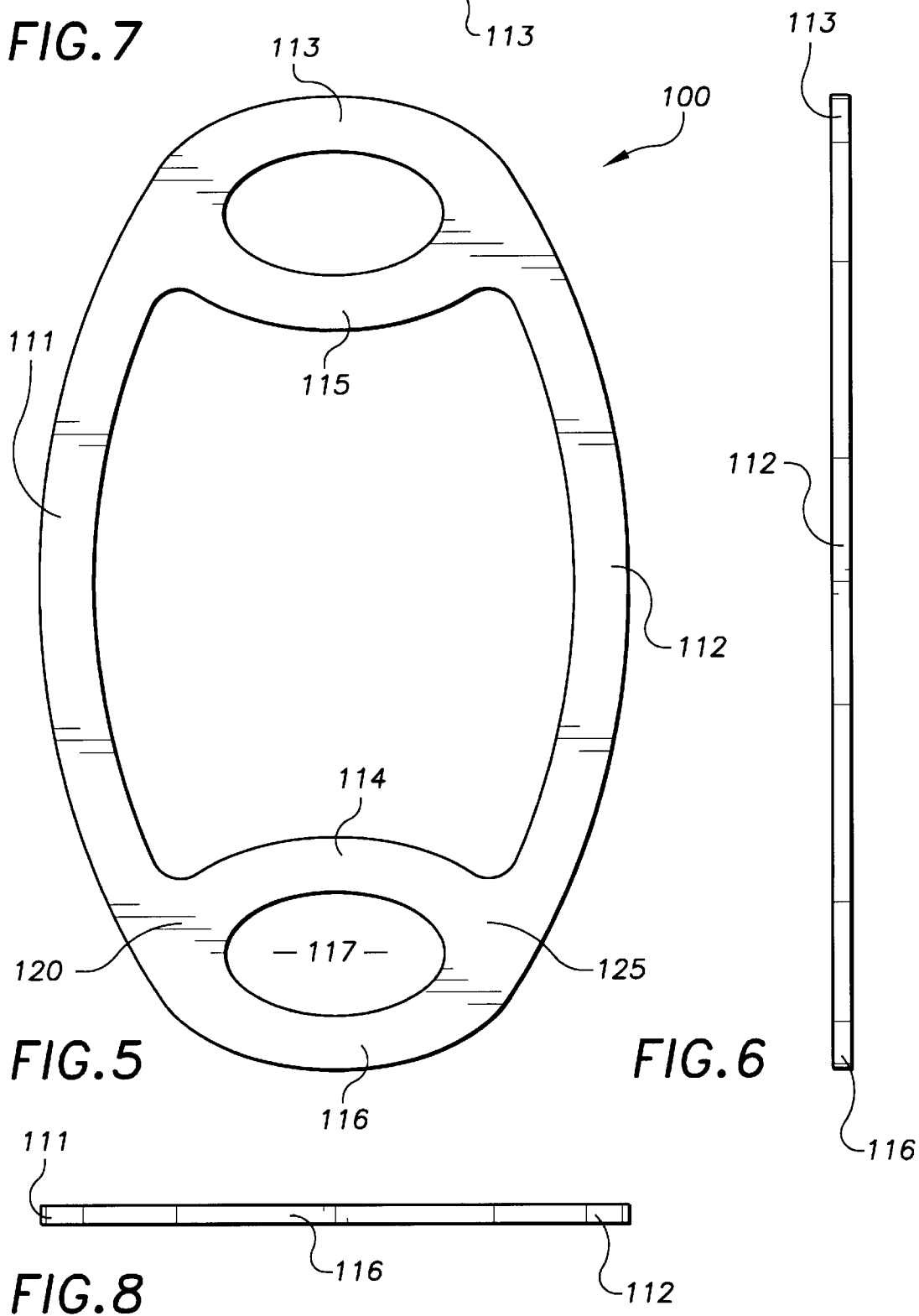

SUPPORTER

CROSS REFERENCE TO RELATED APPLICATION

This application is a continuation of and claims the priority of U.S. Provisional Patent Application Ser. No. 60/113,073 filed Dec. 21, 1998.

FIELD OF THE INVENTION

The present invention is in the field of external medical devices adapted to be worn by a human to support appendages or body parts. The device more particularly is a chin support that retains the mouth of a person closed to enhance breathing through the respiratory passages of the nose. Other human body appendages, such as a finger, thumb, arm, toe, penis and female breasts, can be supported with the device of the invention.

BACKGROUND OF THE INVENTION

Bandages and braces have been designed to keep a person's mouth closed during sleep and cause respiration to ensue exclusively through the nostrils during sleep. The nose and throat airways are the natural channels for respiration. A number of persons have developed the habit of using the mouth as an airway to the throat air passage which causes undue absorption of infectious airborne germs and particulates, dryness in the mouth, and snoring. An example of a head bandage to maintain a person's mouth closed is described by J. S. Baughman in U.S. Pat. No. 649,896.

A recent prior art appliance for preventing snoring and obstructive sleep apnea is disclosed by C. D. Anderson in U.S. Pat. No. 5,893,365 The background of the invention of U.S. Pat. No. 5,893,365 contains a detailed description of the conditions that predicate the problem of snoring and obstructive sleep apnea and methods and devices that mitigate and control snoring and sleep apnea.

SUMMARY OF THE INVENTION

The device of the invention is a supporter for human body appendages or parts that surround the appendage and applies pressure around the appendages to hold the appendages in desired positions. The supporter is a simple, cost effective and conservative medical device for the human chin, jaw, finger, thumb, foot, toe, arm, penis and female breasts.

When applied to a person's chin the supporter alleviates airway obstruction that may occur in a variety of situations such as sleep apnea, transport of unconscious persons and sedated persons. The obstruction of the airway passages is caused by a decrease in tone or relaxation of the muscles of the pharynx, mandible, and neck. The effect of this decrease is a collapsing inward and narrowing of the upper airway passages and the falling back of the tongue to occupy the pharyngeal air passage. There is a decrease in the activity of the genioglossus muscle that connects the base of the tongue to the point of the chin. This can cause snoring and airway passage obstruction or sleep apnea.

When the nasal passages are closed, the user breathes through the mouth. The nose airway passages remain congested while the interior of the mouth, tongue and lips become dry. Mouth breathing bypasses the natural filtration in the nose and reduces the sense of smell. The supporter applies pressure on the chin which retains the user's mouth closed so that air flows through the nasal airway passages. The natural structure of the nose filters the air to remove foreign particulates that can harm lung tissues. The air flowing in the nasal airway passages also relieves nasal congestion and improves the quality of sleep. The supporter when placed about a user's head relaxes the bones, joints, and muscles of the person's face to alleviate temporomandibular joint dysfunction.

The supporter includes a comfortable one-piece elastic member that in one usage fits around the face and chin of a human to overcome breathing and snoring problems. The elastic member keeps the mouth closed during the sleep state when snoring commonly occurs. While awake, the elastic member allows the user to breathe through the mouth talk., eat. drink or cough. The elasticity of the member allows a user with any head circumference and any shape of chin to use it comfortably. The supporter has no projecting structures on the side of the head that can cause the user discomfort while sleeping on the side or stomach. The lower portion of the elastic member has an opening for the chin to locate the chin and throat restraint members around the chin whereby the chin restraint members cannot be dislodged by the user toward the throat when the user moves during sleep. The elastic member is simple to construct, inexpensive, easy and safe to use, comfortable and effective.

The supporter has a lower first elastic member that fits under the chin that applies an upward force on the bottom of the chin to lift the tongue from the posterior pharyngeal wall to open the airway passage and retain the passage open. A front second elastic member joined to opposite portions of the lower elastic member extends across the front of the chin to retain the lower elastic member under the chin and forward of the user's throat. Side straps connected to the front and lower members extend upwardly adjacent opposite sides of the person's face and join with a top member that extends over the top of the person's head to retain the supporter on the head and apply pressure to the bottom of the chin. A pair of top members attached to the straps is used as an alternative to hold the supporter on a person's head. The straps that extend over the head can be provided with releasable connectors, such as Velcro fasteners, to allow adjustment of the supporter to fit different sizes and shapes of human heads.

DESCRIPTION OF THE DRAWINGS

FIG. 5 is a front elevational view of a first modification of FIG. 1;

FIG. 6 is a side view of FIG. 5;

FIG. 7 is a top plan view of FIG. 5;

FIG. 8 is a bottom view of FIG. 5;

DESCRIPTION OF PREFERRED EMBODIMENTS

Figure 3:
FIG. 3 is a top plan view thereof.

Referring to FIGS. 1 to 4, there is shown a human appendage supporter 10 of the invention. Supporter 10 is described as a device to apply a force to the lower portion of a user person's chin and retain the person's mouth closed. Supporter 10 inhibits closing the nasal airway passages, reduces nasal congestion, and mitigates sleep apnea and snoring. The flow of air in the throat is not restricted. The invention is adaptable to support other human body appendages, including but not limited to a finger, thumb, arm, toe, foot, penis and female breasts.

Supporter 10 is a one-piece elastic member of biocompatible material having elastic side straps 11 and 12 joined to an arcuate top member 13. The lower ends of side straps 11 and 12 are joined to an upwardly curved front member 14 and a downwardly curved bottom member 16. Members 14 and 16 have arcuate end portions 20 and 25 that join opposite ends of members 14 and 16. The end portions 20 and 25 are joined to the lower ends of side members 11 and 12. An ovaloid opening 17 for the chin of a person is located between upper and lower members 14 and 16. The upper ends of side straps 11 and 12 and top member 13 have an arcuate convex shape. The arc has about a 60-degree radial apex angle and a chord equal to the radius of the arc. The tangent at each end of the chord is about 30 degrees. This arrangement of the curvature of top member 13 provides uniformity in the stress and loads applied to side straps 11 and 12 and minimizes tearing and ripping of the juncture of straps 11 and 12 and top member 13. The arcs of end portions 20 and 25 and straps 11 and 12 each have a 60 degree arc to enhance the tear strength of the juncture of straps 11 and 12 and chin member 14. The oval opening 17 has arcuate ends with about 60 degree arcs which enhance the tear strength of member 16 and limit rearward movement of member 16 toward a person's throat.

Figure 13:
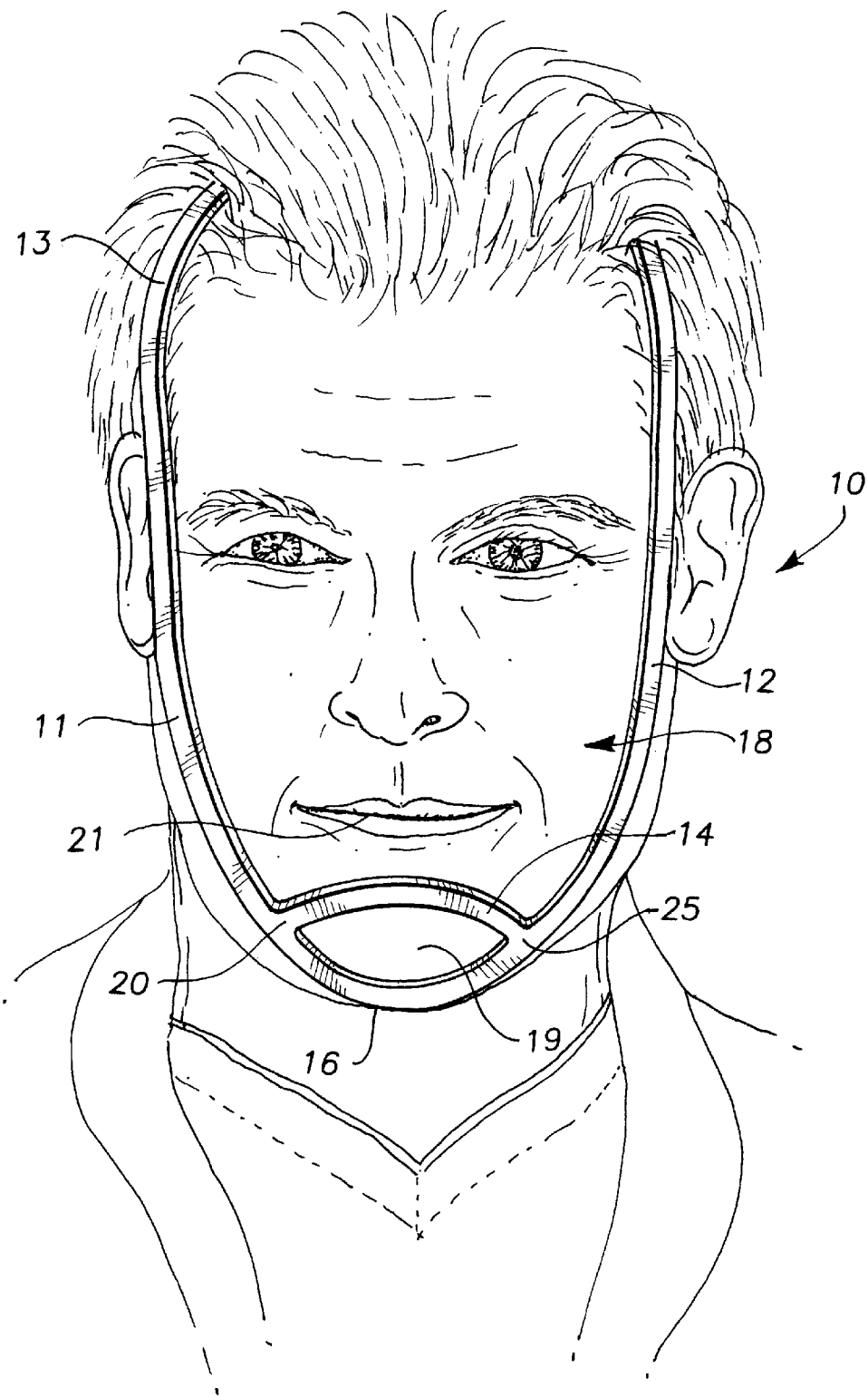
FIG. 13 is a front face view of a person wearing the supporter of FIG. 1.

Elastic side straps 11 and 12 have lengths to allow device 10 to fit around the face of a human 18 with chin 19 located in opening 17, as shown in FIG. 13. The elastic side straps 11 and 12 bias the bottom of chin 19 upward which keeps teeth and mouth 21 closed. This mitigates dry mouth, snoring, growling, and congestion of nasal passages. Upper chin member 14 has a length which locates the lower chin member 16 under the middle section of a person's jaw forward of the jaw joints. The length of member 14 cooperates with the arcuate shapes of end portions 20 and 25 of members 14 and 16 to prevent member 16 from moving back to a person's throat and apply pressure on the throat. Member 16 does not restrict the flow of air through a person's throat. Side members 11 and 12 extended along opposite sides of a person's face apply constant and uniform inward pressure to face skin and muscles. This pressure mitigates pain, relaxes muscle spasms and enhances blood circulation to the jaw bones, joints and face muscles. Additional human benefits include enhancing taste and smell senses, improving character of sleep, reducing fatigue and sleepiness during the day, and improving concentration and work performance. Foreign materials dust, dirt and bacteria do not enter the body via the closed mouth. The air flows through the nasal airway passages into and out of the lung cavities. The natural tissues and structures in the nose filter the air. The air flowing through the nasal airway passages reduces fluid congestion in these passages.

Figures 1, 2:
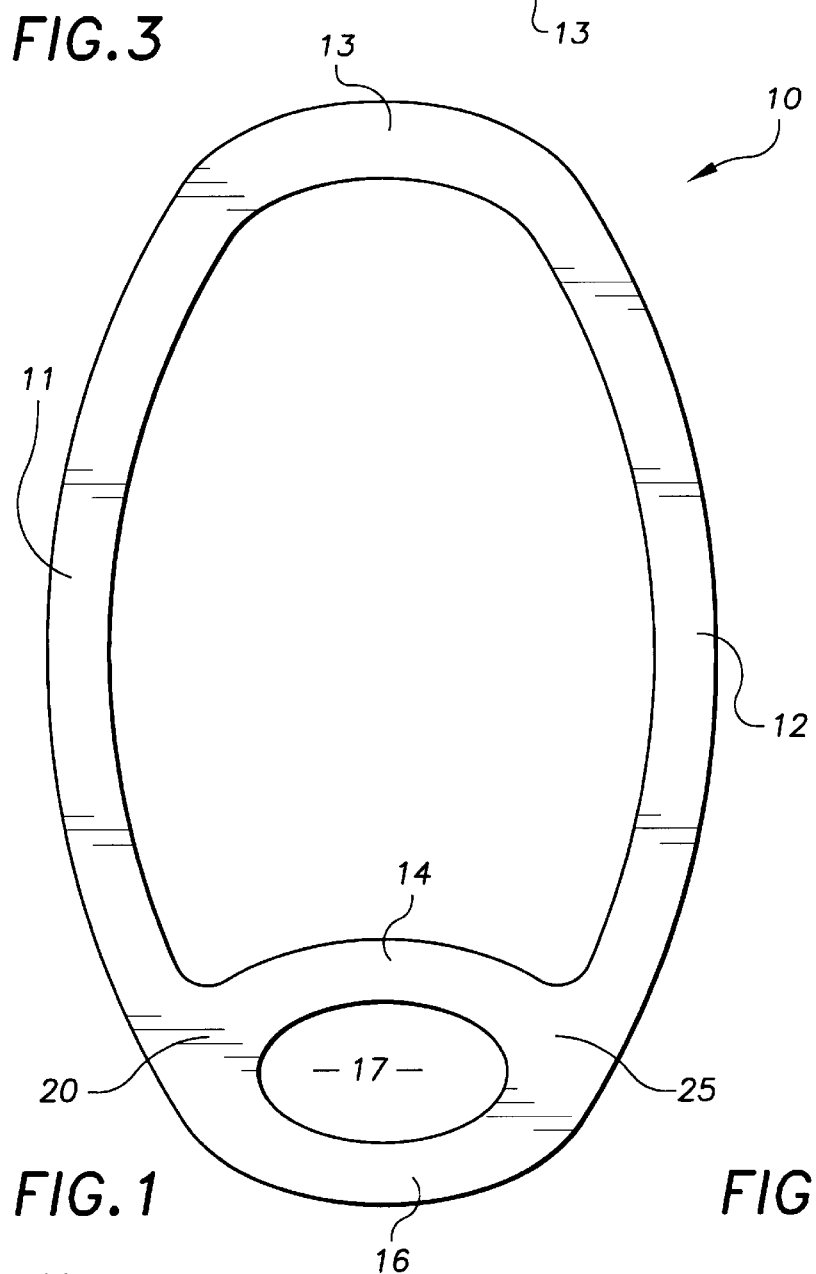
FIG. 1 is a front elevational view of the supporter invention.
FIG. 2 is a side view thereof.
Figure 4:
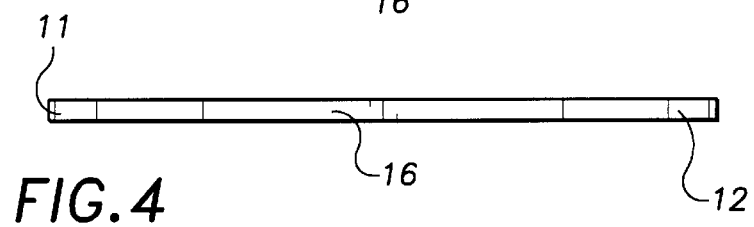
FIG. 4 is a bottom plan view thereof.
Figure 12:
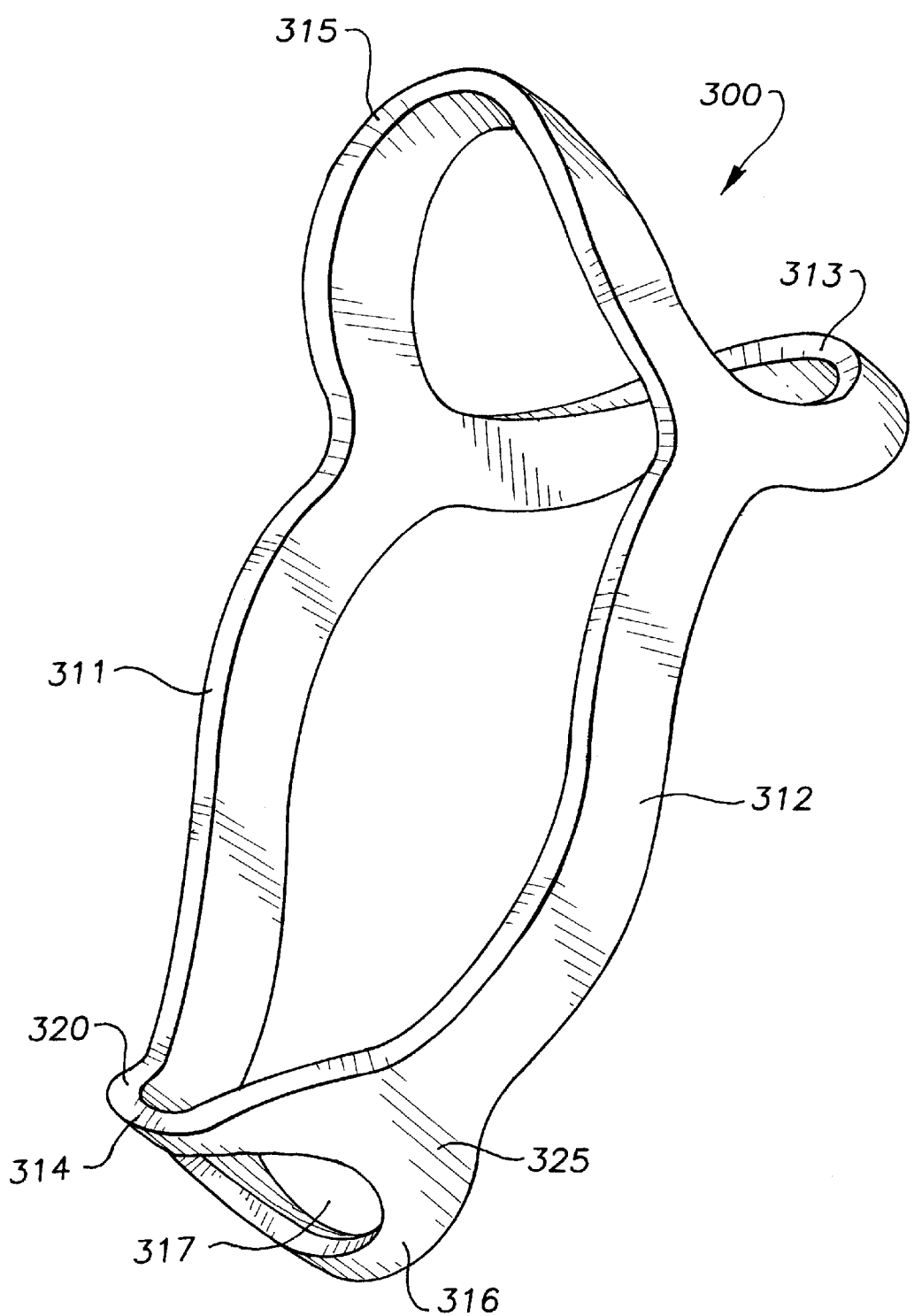
FIG. 12 is a perspective view of a third modification of the supporter of FIG. 1.

The one-piece member of supporter 10 can be made of elastic rubber, silicone rubber, plastic or fabric that is compatible with human body tissue and does not irritate a person's skin. A coating of soft material can be applied to the elastic material. Supporter 10 is die cut from a flat, flexible, and elastic sheet member. The flat supporter 10 changes its shape when used on a person's head to conform to a person's head as shown in FIG. 13. Supporter 10 can be formed in a mold adapted to accommodate plastic. FIG. 12 illustrates a supporter 100 formed in a mold. Flexible and elastic fabric can be cut according to the pattern of supporter 10 as shown in FIG. 1.

A first modification of the supporter 100 is shown in FIGS. 5 to 8. Supporter 100 has convex curved elastic side straps 111 and 112 joined to a pair of arcuate top members 113 and 115. Top members 113 and 115 have a combined generally oval shape that fit over spaced portions of the top or crown of a person's head. The generally oval arrangement of members 113 and 115 reduces movement and slippage of the members 113 and 115 on a person's head.

The arcs between side straps 111 and 112 and members 114 and 115 have about 60 degree radial apex angles to provide uniformity in the stress and loads applied to side straps 111 and 112 and minimize tearing and ripping of the juncture of straps 111 and 112 and members 114 and 115. The lower ends of straps 111 and 112 are joined to a pair of convex curved front and bottom members 114 and 116. Members 114 and 116 have arcuate end portions 120 and 125 that join opposite ends of members 114 and 116. The end portions 120 and 125 are joined to the lower ends of side members 111 and 112. A chin opening 117 is located between members 114 and 116. The front member 114 has a length which locates the lower member 116 under the middle section of a person's jaw forward of the jaw joints. The length of member 114 cooperates with end portions 120 and 125 to prevent member 116 from moving back toward a person's throat and applying pressure on the throat. The flow of air in the throat is not restricted by supporter 100. Elastic side members 111 and 112 positioned along opposite sides of a person's face apply constant and uniform inward or squeezing pressure to face skin and muscles. This pressure mitigates pain, relaxes muscle spasms and enhances blood circulation to the jaw bones, joints and face muscles.

Figure 9:
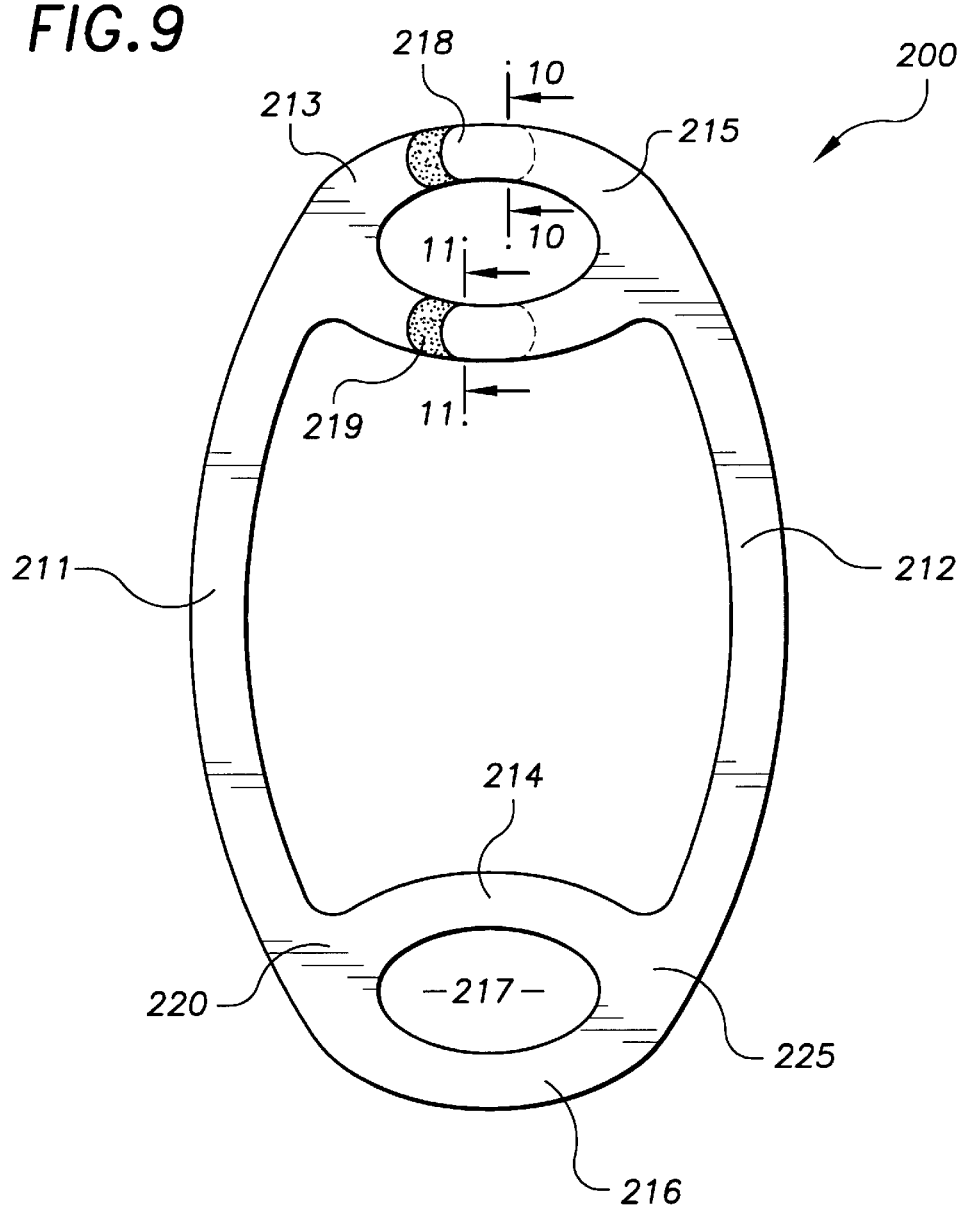
FIG. 9 is a front elevational view of a second modification of FIG. 1.
Figure 10:
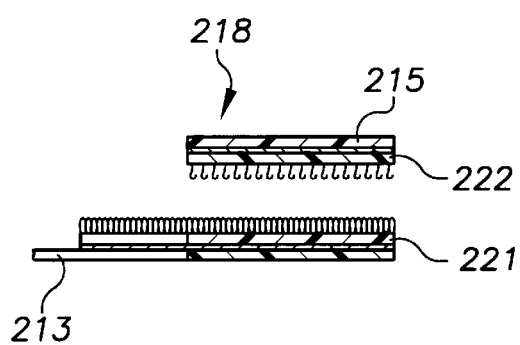
FIG. 10 is a separated sectional view taken along the line 10—10 of FIG. 9.
Figure 11:
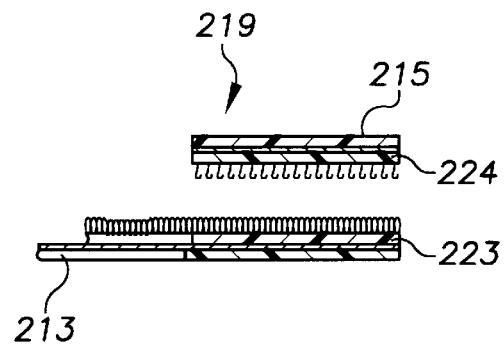
FIG. 11 is a separated sectional view taken along the line 11—11 of FIG. 9.

A second modification of the supporter, indicated generally at 200, shown in FIG. 9, has a shape and materials similar to supporter 100. Supporter 200 has elastic side straps 211 and 212 joined to a pair of curved front and bottom members 214 and 216. Members 214 and 216 have arcuate end portions 220 and 225 that join opposite ends of members 214 and 216. The end portions 220 and 225 are joined to the lower ends of side members 211 and 212. A chin opening 217 is located between members 214 and 216. The upper ends of straps 211 and 212 are joined to Y-shaped ends 213 and 215. Releasable connectors 218 and 219, such as hook and loop releasable fasteners, join Y-shaped ends 213 and 215. As shown in FIG. 10, connector 218 has a fiber loop pad 221 attached to member 213 and a fiber hook pad 222 attached to member 215. Connector 219, shown in FIG. 11, has a fiber loop pad 223 secured to member 213 and a fiber hook pad 224 attached to member 215. Pads 221, 222, 223 and 224 can be secured with an adhesive or stitched to members 213 and 215. The loop and hook structures of connectors 218 and 219 allow adjustment of supporter 200 on a person's head. The size of supporter 200 can be changed to fit different head types. The tension and jaw holding forces can also be adjusted by changing the positions of connectors 218 and 219.

A third modification of the supporter, indicated generally at 300, shown in FIG. 12, has elastic side straps 311 and 312 joined to head members 313 and 315 and chin members 314 and 316. Supporter 300 is a one-piece elastic member formed by molding plastic, rubber, and like elastic materials, lead members 313 and 315 joined to the upper ends of side members 311 and 312 extend in opposite directions. The arcs between head members 313 and 315 have broad convex curvatures which reduce stress points and mitigate against tearing of the members 313 and 315 from each other. The arcs at the junctures of side members 311 and 312 and members 313, 315, 314 and 316 are also broad to prevent tearing of the supporter 300 in use. Members 314 and 316 have arcuate end portions 320 and 325 that join opposite ends of members 314 and 316. The end portions 320 and 325 are joined to the lower ends of side members 311 and 312. The arcs preferably have 60-degree radial apex angles as described with reference to supporter 10. The upper chin member 314 above oval chin opening 317 has a length which locates the lower chin member 316 under the middle section of a person's jaw forward of the jaw joints. The length of member 314 cooperates with end portions 320 and 325 to prevent member 316 from moving back to a person's throat and apply pressure on the throat. The position of member 316 is maintained under the chin so that it does not restrict the flow of air through a person's throat. Side members 311 and 312 when placed on a person's head are located adjacent opposite sides of the person's face and apply constant and uniform pressure to face skin and muscles. This pressure reduces face pains, relaxes muscle spasms and enhances blood circulation to the jaw bones, joints and face muscles.

Supporters 10. 100, 200 and 300 bias the humanoid lower mandibular and retain the mouth shut, teeth closed, and nasal airway passages open. The elastic side members exert a continuous force up to 2 pounds on the lower jaw of the person using the devices to maintain the person's mouth closed and inhibit the tongue from moving back into the person's throat. The elastic side members also apply inward pressure to opposite sides of a person's face to mitigate stress and pain in facial muscles and joints. The benefits of these devices while asleep include nasal congestion relief, dry mouth prevention, tooth decay reduction, saliva retention, snore and involuntary verbal expression mitigation, and nasal air filtration. Continuous use of these devices establishes a relearning process whereby a person continues to breathe through the nose.

There has been disclosed several embodiments of the supporter of the invention. Changes in the structures, material, and arrangement of structures can be made by persons skilled in the art without departing from the invention.

What is claimed is:

1. A supporter for an appendage of a human comprising: a one-piece elastic means for holding the appendage in a selected position, said elastic means having first and second side members having upper and lower ends and elongated convex shapes, a pair of members joined to the lower ends of the side members, said pair of members being spaced from each other to accommodate a portion of an appendage of a human, said pair of members having adjacent arcuate end portions joined together to the lower ends of the side members, one of said pair of members having a length cooperating with the arcuate end portions to maintain the other of said pair of members on the appendage, and means joined to the upper ends of the side members engageable with a portion of a person to retain the pair of members on the appendage.

2. The supporter of claim 1 wherein: said first and second side members are elongated flat elastic members.

3. A supporter for an appendage of a human comprising: a one-piece elastic means for holding the appendage in a selected position, said elastic means having first and second side members having upper and lower ends, a pair of members joined to the lower ends of the side members, the pair of members having arcuate shapes surrounding an oval opening for accommodating an appendage of a human, said pair of members having adjacent arcuate end portions joined together to the lower ends of the side members, one of said pair of members having a length cooperating with the arcuate end portions to maintain the other of said pair of members on the appendage, and means joined to the upper ends of the side members engageable with a portion of a person to retain the pair of members on the appendage.

4. The supporter of claim 2 wherein: the means joined to the upper ends of the side members comprises an arcuate top member.

5. A supporter for an appendage of a human comprising: a one-piece elastic means for holding the appendage in a selected position, said elastic means having first and second side members having upper and lower ends, a pair of members joined to the lower ends of the side members, said pair of members being spaced from each other to accommodate a portion of an appendage of a human, said pair of members having adjacent arcuate end portions joined together to the lower ends of the side members, one of said pair of members having a length cooperating with the arcuate end portions to maintain the other of said pair of members on the appendage, and means joined to the upper ends of the side members engageable with a portion of a person to retain the pair of members on the appendage, the means joined to the upper ends of the side members comprising a pair of spaced members having arcuate end portions joined to the upper ends of the side members, the arcuate end portions joined to the lower ends of the side members each having an arc of about a 60-degree radial apex angle.

6. The supporter of claim 5 wherein: the pair of spaced members joined to the upper ends of the side members each have arcuate shapes.

7. The supporter of claim 5 wherein: each of said pair of spaced members joined to the upper ends of the side members have releasable connectors for selectively changing the lengths of the pair of spaced members thereby altering the size of the supporter to fit different sized human heads.

8. The supporter of claim 5 wherein: said first and second members, the pair of spaced members, and the means joined to the upper ends of the side members are coplanar.

9. The supporter of claim 5 wherein: said one-piece elastic means is molded elastic material.

10. A supporter for holding a person's mouth closed, said person having a chin, face and head, comprising: a one-piece elastic means engageable with a person's chin and head to hold the person's mouth closed, said elastic means having first and second elastic side members having elongated convex shapes, each of said side members having upper and lower ends, upper and lower chin members spaced from each other adapted to fit around the person's chin, said chin members having arcuate end portions joined to the lower ends of the first and second side members, said upper chin member having a length which cooperates with the arcuate end portions to maintain the lower chin member forwardly of the person's throat whereby the lower chin member does not interfere with air flow in the person's throat, and means joined to the upper ends of the side members engageable with person's head to retain the chin members about the person's chin to maintain the person's mouth closed.

11. The supporter of claim 10 wherein: said first and second side members are elongated flat elastic members.

12. A supporter for holding a person's mouth closed, said person having a chin, face and head, comprising: a one-piece elastic means engageable with a person's chin and head to hold the person's mouth closed, said elastic means having first and second elastic side members, each of said members having upper and lower ends, upper and lower chin members spaced from each other having arcuate shapes surrounding an oval opening adapted to fit around the person's chin, said chin members having arcuate end portions joined to the lower ends of the first and second side members, said upper chin member having a length which cooperates with the arcuate end portions to maintain the lower chin member forwardly of the person's throat whereby the lower chin members does not interfere with air flow in the person's throat, and means joined to the upper ends of the side members engageable with the person's head to retain the chin members about the person's chin to maintain the person's mouth closed.

13. The supporter of claim 10 wherein: the means joined to the upper ends of the side members comprises an arcuate top member.

14. A supporter for holding a person's mouth closed, said person having a chin, face and head, comprising: a one-piece elastic means engageable with a person's chin and head to hold the person's mouth closed, said elastic means having first and second elastic side members, each of said side members having upper and lower ends, upper and lower chin members spaced from each other adapted to fit around the person's chin, said chin members having arcuate end portions joined to the lower ends of the first and second side members, said upper chin member having a length which cooperates with the arcuate end portions to maintain the lower chin member forwardly of the person's throat whereby the lower chin member does not interfere with air flow in the person's throat, and means joined to the upper ends of the side members engageable with the person's head to retain the chin members about the person's chin to maintain the person's mouth closed, the means joined to the upper ends of the side members comprises a pair of spaced members having arcuate end portions joined to the upper ends of the side members, each of said pair of spaced members joined to the upper ends of the side members having releasable connectors for selectively changing the lengths of the pair of spaced members thereby altering the size of the supporter to fit different sized human heads.

15. The supporter of claim 14 wherein: the pair of spaced members joined to the upper ends of the side members each have arcuate shapes.

16. The supporter of claim 14 wherein: said first and second members, the pair of spaced members, and the means joined to the upper ends of the side members are coplanar.

17. The supporter of claim 14 wherein: said one-piece elastic means is molded elastic material.

18. The supporter of claim 14 wherein: the arcuate end portions of the chin members each have an arc of about a 60-degree radial apex angle.

* * * * *